(12) United States Patent
Sprong et al.

(10) Patent No.: US 9,370,084 B2
(45) Date of Patent: Jun. 14, 2016

(54) DETERMINING CHANGES IN THE X-RAY EMISSION YIELD OF AN X-RAY SOURCE

(75) Inventors: Hans Peter Sprong, Eindhoven (NL); Martin Kimutai Duerr, Aachen (DE); Rainer Kiewitt, Roetgen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 221 days.

(21) Appl. No.: 13/883,291

(22) PCT Filed: Nov. 2, 2011

(86) PCT No.: PCT/IB2011/054871
§ 371 (c)(1),
(2), (4) Date: May 3, 2013

(87) PCT Pub. No.: WO2012/069944
PCT Pub. Date: May 31, 2012

(65) Prior Publication Data
US 2013/0223594 A1    Aug. 29, 2013

(30) Foreign Application Priority Data
Nov. 8, 2010  (EP) .................................. 10190389

(51) Int. Cl.
*H05G 1/54*    (2006.01)
*H01J 35/02*    (2006.01)
(Continued)

(52) U.S. Cl.
CPC *H05G 1/54* (2013.01); *H01J 35/02* (2013.01); *H05G 1/30* (2013.01); *A61B 6/507* (2013.01)

(58) Field of Classification Search
CPC ..... H01J 35/00; H01J 2235/085; H01J 35/28; H05G 1/2634; H05G 1/54; H05G 1/26; H05G 1/34

USPC .................. 378/145, 151, 148, 108, 110, 112
See application file for complete search history.

(56) References Cited

U.S. PATENT DOCUMENTS 4,172,223 A * 10/1979 Ishijima et al. ............... 378/108
4,321,471 A    3/1982 Holland et al.
(Continued)

FOREIGN PATENT DOCUMENTS

DE      2124035      11/1972
JP      54090985      7/1979
(Continued)

OTHER PUBLICATIONS

English translation of Japanese patent application JP 11-244275-A.*
(Continued)

*Primary Examiner* — Glen Kao
*Assistant Examiner* — Chih-Cheng Kao (57) ABSTRACT

The present invention relates to determining changes in the X-ray emission yield of an X-ray tube, in particular determining dose degradation. In order to provide determination of such changes, an X-ray source is provided comprising a cathode, an anode; and at least one X-ray sensor (16). The cathode emits electrons towards the anode and the anode comprises a target area on which the electrons impinge, generating X-ray radiation. An X-ray barrier (24) is provided with an aperture (26) for forming an emitting X-ray beam from the X-ray radiation, wherein the emitting X-ray beam has a beam formation (30) with a central axis. The at least one X-ray sensor is arranged within the beam formation and measures the X-ray intensity for a specific direction of X-ray emission with an angle with respect to the central axis. The at least one X-ray sensor can be positioned inside the beam formation (30), but outside the "actual field of view" (40) as determined by a diaphragm (36).

22 Claims, 8 Drawing Sheets

(51) Int. Cl.
*H05G 1/30* (2006.01)
*A61B 6/00* (2006.01)

(56) References Cited

U.S. PATENT DOCUMENTS

| | | | |
|---|---|---|---|
| 4,763,343 A * | 8/1988 | Yanaki | 378/110 |
| 5,867,553 A * | 2/1999 | Gordon et al. | 378/146 |
| 6,542,576 B2 | 4/2003 | Mattson | |
| 7,020,243 B2 * | 3/2006 | Hsieh | 378/62 |
| 8,009,052 B2 * | 8/2011 | Hornig et al. | 340/600 |
| 8,554,902 B2 * | 10/2013 | Ebert et al. | 709/224 |
| 2003/0138079 A1 | 7/2003 | Schmitt | |
| 2004/0109536 A1 | 6/2004 | Shefer et al. | |
| 2005/0163284 A1 | 7/2005 | Inazuru | |
| 2009/0067578 A1 | 3/2009 | Behling et al. | |
| 2010/0067655 A1 * | 3/2010 | Yamaguchi et al. | 378/62 |

FOREIGN PATENT DOCUMENTS

| | | |
|---|---|---|
| JP | 6132998 A | 2/1986 |
| JP | 11244275 | 9/1999 |
| JP | 2006149493 A | 6/2006 |

OTHER PUBLICATIONS

Translation of JP 61-032998 A (Feb. 15, 1986).*

Fritz Et All, "A Comparison of Computer and Measured Heel Effect for Various Target Angles", Med. Phys. vol. 9, No. 2, 1982, pp. 216-219.

Erdelyi et al, "Measurement of the X-Ray Tube Anodes' Surface Profile and Its Effects on the X-Ray Spectra", Medical Physics, vol. 36, No. 2, 2009, p. 587-593.

* cited by examiner

DETERMINING CHANGES IN THE X-RAY EMISSION YIELD OF AN X-RAY SOURCE

FIELD OF THE INVENTION

The present invention relates to determining changes in the X-ray emission yield of an X-ray tube, in particular to determining dose degradation. The invention relates in particular to an X-ray source, an X-ray imaging system, a method for determining changes in the X-ray emission yield of an X-ray source, a computer program element, and a computer-readable medium.

BACKGROUND OF THE INVENTION

In X-ray sources, for example in X-ray tubes, electrons with kilovolt energies impact onto the focal track of an anode, for example a rotating anode, for generating X-ray radiation. This leads among others to modifications of the anode surface. As a consequence, the tube X-ray yield changes over the course of its lifetime, which may have an impact on the X-ray application. In US 2009/0067578 A1, a rotatable anode is described with a structure comprising slits, for example, which structure can be detected if the structure on the anode passes the focal spot. Thus, properties of the focal spot can be determined from changes of the detection signal during operation of the X-ray tube.

SUMMARY OF THE INVENTION

It has been shown that when the tube yield degrades, due to system limits, the X-ray dose emitting from the X-ray source can become too low. Further, it has been shown a calibration procedure to be carried out by service personnel has economic disadvantages and requires long-time planning procedures.

Thus, there may be a need for providing determination of changes in the X-ray emission yield of an X-ray source in order to provide correct dose applications.

The object of the present invention is solved by the subject-matter of the independent claims, wherein further embodiments are incorporated in the dependent claims.

It should be noted that the following described aspects of the invention apply also for the X-ray source, the X-ray imaging system, the method, the program element and the computer-readable medium.

According to an exemplary embodiment of the invention, an X-ray source is provided comprising a cathode, an anode, and at least one X-ray sensor. The cathode emits electrons towards the anode, wherein the anode comprises a target area on which the electrons impinge, generating X-ray radiation. An X-ray barrier is provided with an aperture for forming an emitting X-ray beam from the X-ray radiation. The emitting X-ray beam has a beam formation with a central axis. The emitting beam formation can be viewed as the maximum field of investigation for that X-ray source's configuration. The at least one X-ray sensor is arranged within the beam formation. The at least one X-ray sensor measures the X-ray intensity for a relatively small angular segment in a specific direction of X-ray emission with respect to the central axis.

Such an X-ray source allows determining changes in the X-ray emission yield, because the X-ray sensor is positioned such that X-ray intensity of the X-ray beam can be measured.

According to another exemplary embodiment of the invention, a diaphragm with an opening is provided, which opening defines an actual field of investigation, wherein the at least one X-ray sensor is arranged outside this actual field of investigation.

According to another exemplary embodiment of the invention, the anode and the cathode are arranged inside a vacuum tube, wherein the vacuum tube comprises an X-ray window as the aperture in the X-ray barrier. The at least one X-ray sensor is arranged outside the vacuum tube.

For example, the at least one X-ray sensor is arranged on the outside of the X-ray window.

According to a further exemplary embodiment of the invention, an X-ray imaging system is provided with an X-ray source, a detector, and a processing unit. The X-ray source is provided as an X-ray source according to one of the above mentioned exemplary embodiments, comprising at least one X-ray sensor. The X-ray source is adapted to emit an X-ray beam having a beam formation and a central axis. The at least one X-ray sensor is adapted to measure X-ray intensity for a specific direction of X-ray emission with respect to the central axis. The processing unit is adapted to compare the measured data with stored data and to analyze the measured data, and to determine a dose degradation value based on the analysis. The detector is adapted to record image information of an object of interest.

According to a further exemplary embodiment, a method for determining changes in the X-ray emission yield of an X-ray source is provided, comprising the following steps:
 a) Emitting an X-ray beam with an X-ray source, which X-ray source comprises a cathode to emit electrons towards an anode to generate X-ray radiation, wherein the X-ray beam has a beam formation with a central axis.
 b) Measuring X-ray intensity for a specific direction of X-ray emission with respect to the central axis with at least one X-ray sensor, which X-ray sensor is arranged within the beam formation of the X-ray beam.
 c) Comparing the measured data with stored data and analyzing the measured data.
 d) Determining a dose degradation value based on the analysis of step c).

For example, the measured data is converted into a dose rate output for comparison with stored data and for analyzing the measured data, for instance the electrical power input is taken into account calculated from tube voltage multiplied by average tube current.

According to a further exemplary embodiment, following step d), a step e) is provided comprising calculating new settings of the X-ray source based on the degradation value for further X-ray generating. Further, a step g) is provided comprising updating a yield factor of the X-ray source.

It can be seen as the gist of the invention to measure the X-ray intensity for a specific angle of radiation with a sensor positioned inside the beam formation in order to provide precise information about the changes in the X-ray emission yield, i.e. providing information about dose degradation, for example. The sensor is arranged such that the actual field of view is not affected.

These and other aspects of the invention will become apparent from and elucidated with reference to the embodiments described hereinafter.

BRIEF DESCRIPTION OF THE DRAWINGS

Exemplary embodiments of the invention will be described in the following drawings.

DETAILED DESCRIPTION OF EMBODIMENTS

Figure 1:
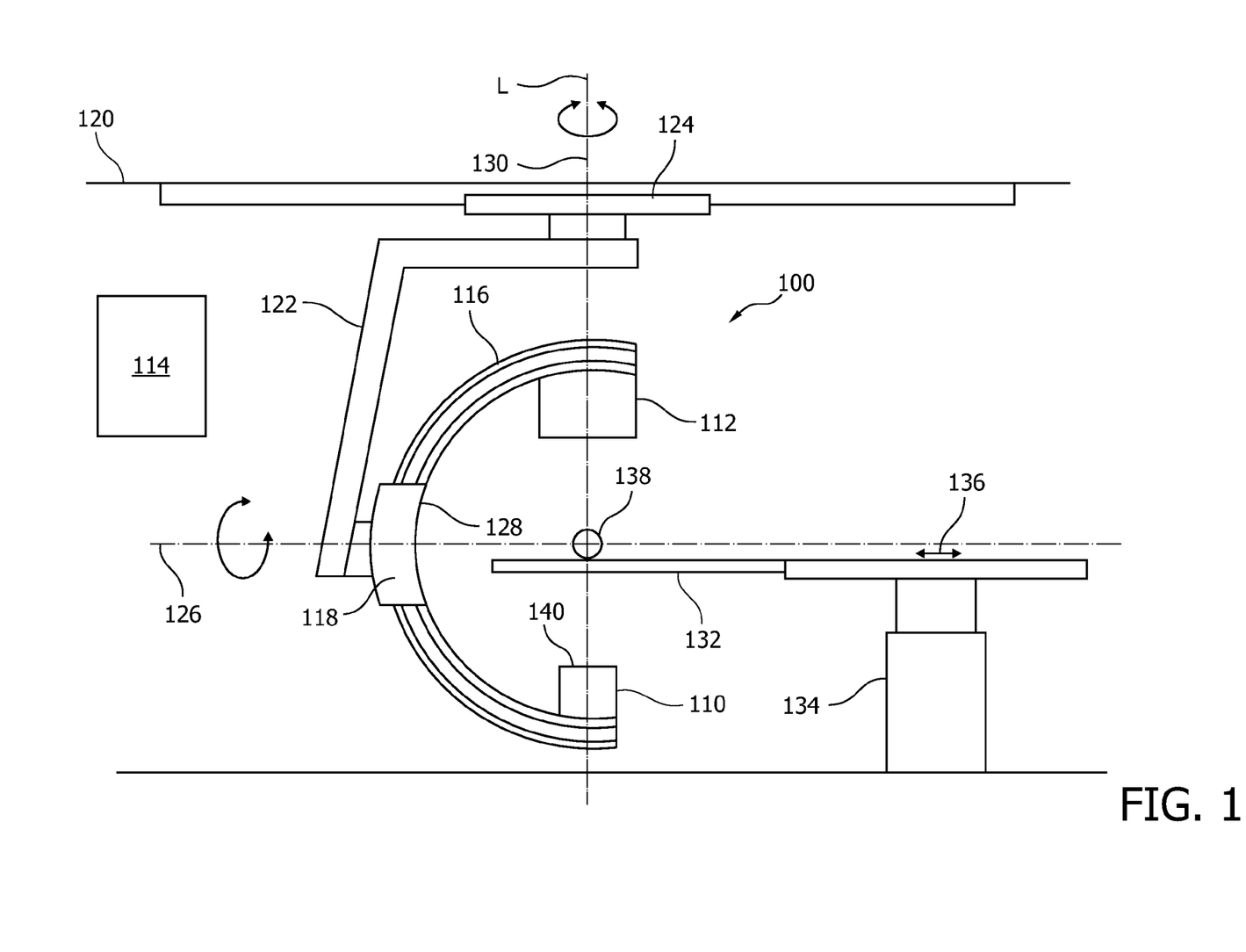
FIG. 1 schematically illustrates an X-ray imaging system according to an exemplary embodiment of the invention.

FIG. 1 schematically illustrates an X-ray imaging system 100 with an X-ray source 110, a detector 112, and a processing unit 114. The X-ray source 110 and the X-ray detector 112 are arranged on opposite ends of a C-arm 116. The C-arm 116 is rotatably supported by a C-arm support 118, which C-arm support 118 is suspended from a ceiling 120 by a rotatable support arm 122. The latter is mounted rotatably to the ceiling 120 by a ceiling mount 124. The C-arm 116 can be rotated around a horizontal axis, indicated with reference numeral 126. Further, the C-arm is slidably movable in a curve-like manner in a sliding support device 128 of the C-arm support 118. The support arm 122 can be rotated around a vertical axis, indicated with reference numeral 130. Thus, the detector 112 and the X-ray source 110 can be brought to a large number of positions with respect to an object to be investigated 138. Further, an object supporting device in form of a table 132 is provided, which table can be adapted in its vertical position by lowering or moving the table upwards by a respective adjustable table stand 134. Further, the table 132 can be moved in a horizontal direction indicated with a double arrow 136. Thus, an object 138 can be placed on the table 132 and arranged such that the object 138 is located between the X-ray source 110 and the detector 112.

The X-ray source comprises a cathode, an anode and at least one X-ray sensor. The cathode emits electrons towards the anode, and the anode comprises a target area on which the electrons impinge, thereby generating X-ray radiation (described further below). Further, an X-ray barrier is provided with an aperture for forming an emitting X-ray beam from the X-ray radiation.

It must be noted that the processing unit 114 is shown only schematically. Of course, the processing unit can be arranged at any convenient place, for example inside an examination laboratory in a hospital.

As will be described with reference to FIG. 2 etc., the X-ray source is adapted to emit an X-ray beam (not further shown) having a beam formation with a central axis.

Further, the X-ray source 110 comprises at least one X-ray sensor 140 (not further shown) which is adapted to measure X-ray intensity for an angle between a specific direction of X-ray emission and the central axis. The X-ray sensor is further arranged within the beam formation.

The processing unit 114 is adapted to compare the measured data with stored data and to analyse the measured data. The processing unit 114 is further adapted to determine a dose degradation value based on the analysis.

Further, the detector 112 is adapted to record image information of an object of interest.

It is noted that the processing unit 114 is connected to the at least one X-ray sensor 140, to the X-ray generator (not shown) controlling the X-ray source 110 and the X-ray detector 112, for example by a cable connection or by a wireless connection. However, these connections are not further shown.

The X-ray source 110 is described in the following with reference to FIG. 2.

Figure 2:
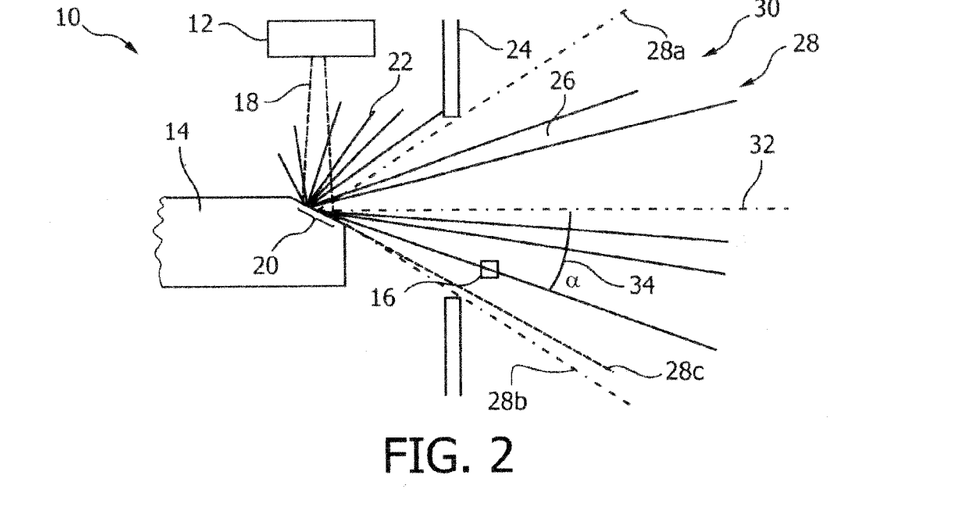
FIG. 2 schematically illustrates a cross-section through an X-ray source according to an exemplary embodiment of the invention.

In FIG. 2, an X-ray source 10 is shown comprising a cathode 12, an anode 14 and at least one X-ray sensor 16.

Figure 2A:
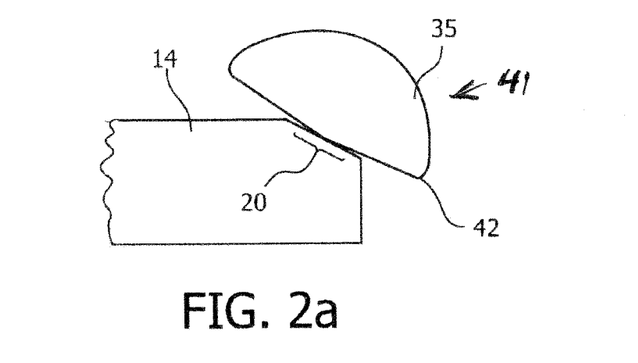
FIG. 2a schematically illustrates a cross-section through the X-ray intensity distribution above a focal spot.

The cathode emits electrons towards the anode, which electrons are schematically illustrated with dotted lines 18. The anode comprises a target area 20 on which the electrons 18 impinge, generating X-ray radiation, indicated with a number of lines 22. The X-ray radiation is emitting in a random way, causing a kidney shaped intensity distribution 35 above the surface of the focal track, illustrated in drawing 2a, which is isotropic at larger angles with respect to the focal track's surface, i.e., in what is intensity-wise the bulk 41 of the X-ray beam 28, but declines steeply with small angles at the "heel" 42. This is called the "heel effect."

Further, an X-ray barrier 24 is provided with an aperture 26 for forming an emitting X-ray beam 28, schematically illustrated with outlines 28a and 28b. The X-ray beam 28 is formed from the X-ray radiation 22.

The emitting X-ray beam 28 has a beam formation 30 with a central axis 32 that runs through the centre of the target area and the centre of the aperture 26. Depending on the configuration of the aperture 26, the beam formation 30 may be further limited 28c by the shade of the anode 14.

Although the actual beam is formed when the X-ray radiation passes the aperture 26, the beam formation reaches also into the area in front of the aperture 26, i.e. in the area before it passes the aperture, since the beam formation 30 is defined by those X-ray radiation lines that start at the target area 20 and reach through the aperture 26.

According to the invention, the at least one X-ray sensor 16 is arranged within the beam formation 30.

The at least one X-ray sensor 16 measures the X-ray intensity for an angle α, indicated with reference numeral 34, between a specific direction of X-ray emission and the central axis 32.

According to a further aspect of the invention, the aperture 26 is arranged for shaping the cross-section of the X-ray beam.

For example, the aperture 26 has a circular shape arranged such that the beam formation 30 has a cone shape, as indicated in the schematic cross-section in FIG. 2.

According to a further exemplary embodiment, the aperture is a slot arranged such that the beam formation has a fan shape (not further shown).

According to a further aspect of the invention, the X-ray barrier 24 is X-ray opaque.

According to a further aspect, the X-ray barrier 24 is X-ray absorbing.

According to a further aspect of the invention, the beam formation 30 is the maximum field of investigation for an X-ray source configured as illustrated.

According to a further aspect, the central axis 32 runs through the centre of the target area 20 also called focal spot.

According to another aspect, the focal spot is the particular area on the target area, onto which the electrons impinge.

According to a further aspect, the difference in intensity between radiation at low angles with respect to the focal track's surface and at higher angles is measurable with two X-ray sensors 16 positioned at different angles or a multi pixel sensor (not shown).

Figure 3:
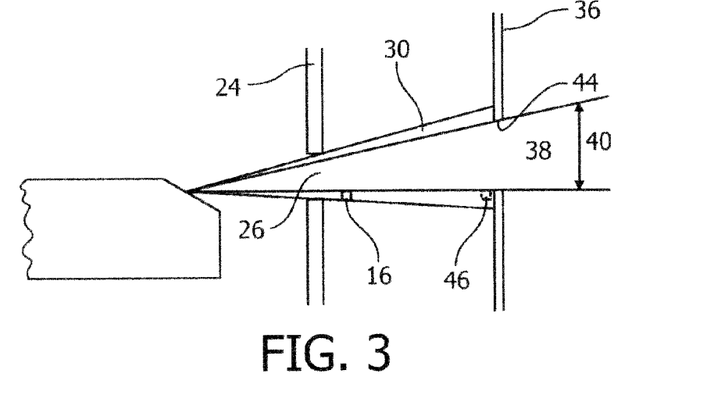
FIG. 3 illustrates a schematic cross-section through a further exemplary embodiment of the invention.

With reference to FIG. 3, according to a further exemplary embodiment, a diaphragm 36 with an opening 38 is provided, which opening defines an actual field of investigation 40, for instance to limit the beam formation to cover only the desired detector size. The at least one X-ray sensor 16 is arranged outside the actual field of investigation 40.

(It is for obvious reasons not legally allowed to radiate outside the limits of the desired detector size).

The actual field of investigation 40 is determined by the area which is being detected by the detector. The actual field of investigation 40 can be as large as the maximum field of investigation 30, but is in practice smaller than this.

According to a further aspect, an actual field of investigation 40 is arranged to be covered by the X-ray beam and the at least one X-ray sensor is arranged outside the actual field of investigation 40.

According to a further aspect of the invention, the field of investigation is also referred to as the field of view, although this field is not actually viewed by the user, but only covered with X-ray radiation and thus made visible. However, since the X-ray radiation passing through the opening 38 provides information detectable by a detector, which are further generated into visible X-ray images, the term field of view also applies.

According to a further aspect, the diaphragm 36 comprises one or more shutters.

According to a further aspect, the diaphragm 36 comprises one or more wedges.

According to a further aspect, the opening 38 is provided for forming an emitting field of investigation X-ray sub-beam having a sub-beam formation.

According to a further aspect, the sub-beam formation is part of the beam formation 30 (not further shown).

According to a further aspect, the at least one X-ray sensor is arranged within the beam formation 30.

For example, the opening 38 is X-ray transparent.

According to a further aspect, the opening 38 is surrounded by an opening edge 44.

According to a further aspect, the at least one X-ray sensor 16 is arranged between the X-ray window 26 and the diaphragm 36.

According to a further aspect, the sensor is mounted on the diaphragm adjacent to the opening edge 44.

According to a further aspect, the actual field of investigation 40 is collimated from the X-ray beam by the diaphragm 36.

According to a further aspect, the at least one X-ray sensor 16 is arranged outside the opening of the diaphragm. This is indicated with a dotted square in FIG. 3, indicated with reference numeral 46.

According to a further aspect, at the diaphragm, the cross-section of the X-ray beam is larger than the opening 38 of the diaphragm 36.

According to a further aspect, the opening is rectangular and the at least one X-ray sensor is arranged within the circular X-ray beam formation, but outside the opening (for further explanation, see FIG. 8 to FIG. 11).

Figure 4:
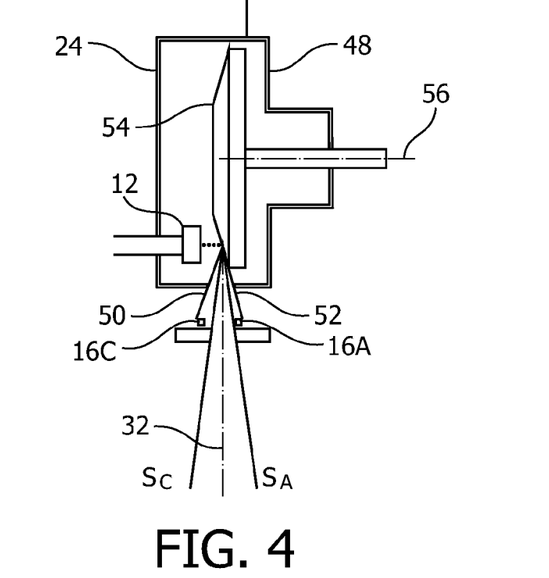
FIG. 4 illustrates a schematic cross-section through a further exemplary embodiment.

According to a further exemplary embodiment of the invention, schematically shown in FIG. 4, the anode and the cathode are arranged inside a tube 48, wherein the tube comprises an X-ray window 50 as the aperture in the X-ray barrier 24. The at least one X-ray sensor is arranged outside the tube.

According to a further exemplary embodiment, the at least one X-ray sensor is arranged inside the tube (not further shown).

According to a further aspect of the invention, the tube 48 is an enclosure providing a vacuum for generating X-ray radiation, e.g. a vacuum tube.

According to a further aspect, the X-ray window 50 is arranged such that a cone-shaped emerging X-ray beam emanates from the tube 48.

For example, the X-ray window 50 has a circular shape.

For example, the at least one X-ray sensor 16 is arranged within the cone-shaped emerging X-ray beam, which emerging X-ray beam is indicated with a cone-shaped dotted outline 52.

According to a further aspect, the at least one X-ray sensor 16 is provided as a single pixel sensor.

As indicated in FIG. 4, according to a further exemplary embodiment, a plurality of single pixel sensors is placed at several positions within the field of X-rays emitted by the X-ray tube.

According to a further exemplary embodiment of the invention, the at least one X-ray sensor is arranged on the outside of the X-ray window 50 (not further shown).

According to a further aspect, at least one X-ray sensor 16 is attached to the surface of the X-ray window 50.

As also indicated in FIG. 4, according to a further aspect, the anode is a rotating anode 54 and the at least one X-ray sensor 16 is positioned towards the anode side with respect to the central axis. As can be seen form FIG. 4, the cathode side is on that side of the central axis 32 that faces the cathode 12. For easier reference, the cathode side is indicated with $S_C$, and the anode side is indicated with $S_A$, i.e. the anode side is on the other side of the central axis 32, i.e. on that side which faces the anode 54.

According to a further aspect of the invention, the at least one X-ray sensor 16 positioned towards the anode side, indicated with reference numeral 16a, is a heel-effect sensor.

According to a further aspect of the invention, the at least one X-ray sensor is positioned towards the cathode side $S_C$ with respect to the central axis 32.

For example, the at least one X-ray sensor 16 towards the cathode side $S_C$ is a general dose sensor indicated with reference numeral 16c.

According to a further aspect, the central axis 32 is perpendicular to the rotating axis of the anode, which rotating axis is indicated with a dotted line 56.

According to a further aspect, at least two sensors are provided, wherein one is positioned on the anode side $S_A$ of the central axis and the other one is positioned on the cathode side $S_C$ of the central axis.

According to a further aspect, the sensor on the anode side is positioned on the lateral side of the field of investigation (see further FIG. 8 to FIG. 11).

According to a further aspect, the sensor on the cathode side is positioned towards or on the cathode side of the field of investigation (see also FIG. 8 to FIG. 11).

According to a further aspect of the invention, a multi-pixel dose sensor 58 is provided, which is described with reference to FIGS. 9 to 11. In the following, an example for generating X-ray radiation is described in detail: One of the common X-ray sources used in medical imaging is the rotating anode X-ray tube. The X-rays are generated by electrons with kilovolt energies impinging on the X-ray target, which in most cases is either a tungsten rhenium alloy or molybdenum. In a tube with a rotating anode, the X-ray target comprises an annular layer of W/Re, respectively Mo, on a disc. For imaging applications, the anode can be slanted by an angle, typically in the range of 7° to 12° at the diameter of the focal track.

Only X-rays emitted within a beam around an axis more or less perpendicular to the rotation axis of the anode are used for the imaging application. The axis more or less perpendicular to the rotation is also referred to as a central axis. In such a configuration, the electrons can be guided onto the focal track with a line focus, hereby reducing the heat load.

Viewing from the central axis onto the slanted anode, the line focus appears with a spot-like shape, because in this projection, the line of the focus electrons shrinks geometrically by a factor of approximately 10.

For X-ray tubes, inherent filtration of X-rays in the X-ray target itself appears. For example, at kilo electronvolt energies, the electrons may penetrate into the target up to several micrometers before converting their entire energy either into heat or X-ray photons. As a result, a fraction of X-rays is generated within the target, i.e. the X-rays have to traverse the bulk of the focal track before reaching the tube's exit window. Such X-rays emanating from within the target may be absorbed on their way to the target surface.

The probability of absorption depends on the path length within the bulk material, such that for longer travelling paths the X-rays are more likely to be absorbed.

Due to the specific geometry of the slanted anode, the inherent filtration depends on the emission direction of X-ray radiation. Moving of the central viewing axis towards the surface of the anode leads to stronger inherent filtration, an effect which is given by the geometry. When the off-axis angle is equal to the anode's slant angle, there is a cut-off in X-ray yield, since this position lies in the shadow of the rotating anode. Thus, an angle-dependent X-ray yield exists, which needs to be accounted for in applications like imaging.

Figure 5:
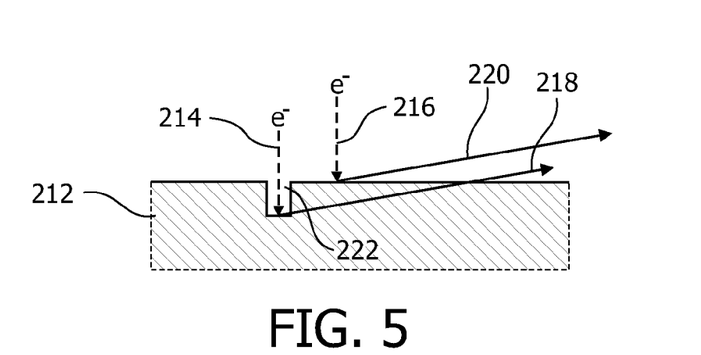
FIG. 5 schematically illustrates aspects of X-ray generation according to an exemplary embodiment.

The focal track on the rotating anode is subject to degradation due to thermal mechanical stress which leads to structural changes of the track surface called "anode roughening." A common phenomenon is crack formation, which causes degradation of tubes' X-ray yield. The reduction of X-ray output by crack formation is caused by the fact that electrons entering the crack generate X-rays deeper in the bulk of the anode. For example, in FIG. 5, a section of an anode 212 is shown onto which electrons impinge, which is indicated with dotted lines 214 and 216. As indicated with further arrows 218 and 220, X-ray photons are generated. However, the electron 214 hits a crack formation 222 in the anode 212. Thus, the X-ray photon is generated at a deeper position within the target material. Thus, the X-ray radiation arrow 218 thus has to pass the material zone of the anode 212 before it reaches the surface of the anode. Contrary to this, the X-ray photon 220 generated by electron 216 is generated in the vicinity of the surface of the anode material. Thus, this photon only travels a very small distance within the anode material before it reaches the surface.

By the increasing number and depths of cracks in the focal track, which is a typical aging effect of rotating anodes, the total X-ray output of a tube is decreased and is accompanied by a change of the emitted X-ray spectrum.

A second effect is that small particles of the anode material will eject from the anode surface covering parts on the inside of the tube including the inside of the aperture 26 reducing its X-ray transparency.

During the lifetime of the X-ray tube, its efficiency deteriorates due to anode roughening and coating of the window, which means a degradation of the tube yield.

For interventional radiography compliance, for example with the entrance dose limitation EDL of the FDA it is essential, in order to remain below the imposed dose limits, that the applied dose is estimated using the tube yield as an input parameter. When the tube yield degrades, the system may limit itself to a dose which is too low. The reduced dose can lead to a deterioration of image quality.

According to an exemplary embodiment of the invention, as already described, the X-ray tube is equipped with one or more X-ray sensors 16 which determine the dose degradation at different angular positions. Thus, the X-ray sensors can also be sensitive to the heel-effect.

For example, the relative dose is measured at different positions, and is therefore less sensitive to variations of the absolute dose.

A further advantage in relying on a relative dose is the independence on the exposure time, which may cause problems in absolute dose measurements in particular for pulsed mode tube operation as used in fluoroscopy.

As a result, the dose degradation can be monitored during normal operation and specific calibration runs become unnecessary.

Figure 6:
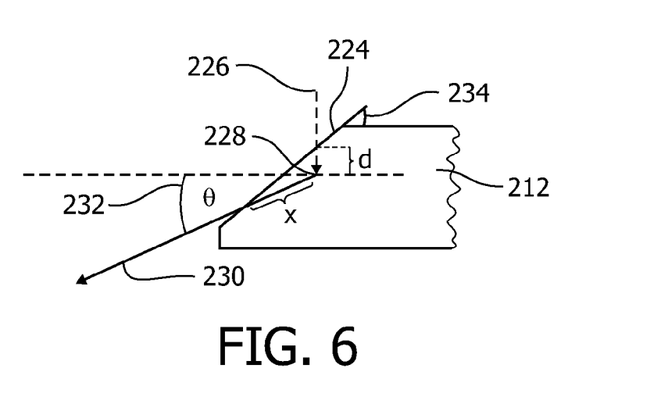
FIG. 6 schematically illustrates further aspects of X-ray generation according to an exemplary embodiment.

In the following, the sensitivity of the anode age sensor described above is explained with reference to FIG. 6, in which by a simple physical model, the heel-effect shall be explained. In FIG. 6, an anode portion 212 with a slanted surface 224 is shown. Electrons 226 impinge on the slanted surface 224 in the area of a target area 228 (not further shown). Due to crack formation for example, the electron reaches a certain depth, indicated with reference letter d, before X-ray radiation is generated, which X-ray radiation is indicated with an arrow 230.

As can be seen, the X-ray radiation has a path portion within the material of the anode 212 and a portion outside the material of the anode 212.

The path length within the X-ray target, i.e. the anode 212, which path length is referred to by the reference letter s, can be expressed as a function of penetration depth d at which the respective photon was generated and the off-axis angle θ, indicated with reference numeral 232. The following equation applies:

$$s(\theta) = d^* \cos(\alpha)/\sin(\theta+\alpha)$$

where α is the anode angle. The anode angle α is indicated with reference numeral 234. The X-ray intensity at the passage over the path length s through matter with density p is described by an attenuation law:

$$I/I_0 = \exp(-\mu^* s)$$

Here, μ is the material specific mass attenuation coefficient which is energy dependent. The inherent filtration of X-ray, which is produced at depth d within the target, therefore leads to an attenuated X-ray flux I/I0 emanating from the target of:

$$I/I_0 = \exp(-\mu^* d^* \cos(\alpha)/\sin(\theta+\alpha))$$

which is dependent on the emission angle. The above-mentioned equation qualitatively describes the heel-effect. The functional dependence of the inherent attenuation leads to an increased sensitivity to the variation of the penetration depth d in particular for off-axis positions towards the surface of the anode, i.e. at angles where the heel-effect strongly reduces the X-ray yield.

Therefore, the X-ray flux at this off-axis position is very sensitive to crack formation, since here, the X-rays are generated at deeper positions within the bulk of the thermal track and the penalty of inherent attenuation is larger.

Figure 7:
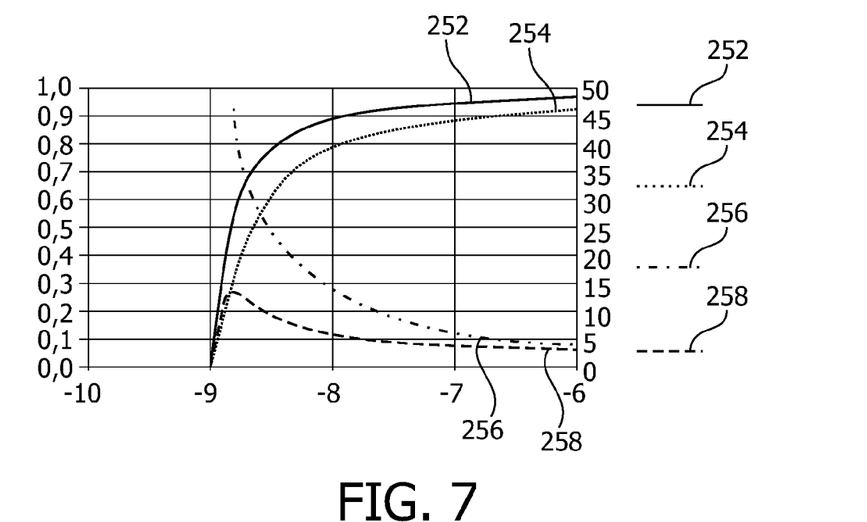
FIG. 7 schematically shows a graph illustrating simulation of X-ray attenuation according to the invention.

In FIG. 7, a simulation of X-ray attenuation of 30 keV X-ray photons generated at a certain depth d within a slanted anode with 9° anode angle is shown (solid and dotted curve). The reduction of the X-ray yield and the cut-off towards emission angles $-\theta=\alpha$ is characteristic for the heel-effect. A variation of the depth d has the strongest effect on the X-ray yield at angles towards the cut-off position (dashed and dashed dotted curve). In FIG. 7, in the vertical axis, the X-ray yield is indicated from range 0 to 1. On the horizontal axis, the off-axis angle $\theta$ (deg) is indicated from $-10$ to $-6$, as an example. On the right vertical side, the relative difference in percentage is indicated with a range from 0 to 50%. In a first line, which is shown as a solid line 252, the following applies: $I/I\_0$ (d=5 μm).

In a second line shown as a dotted curve 254, $I/I\_0$ (d=10 μm) applies.

Further, a third line shown as a dashed curve 256 indicates the absolute reduction of X-ray yield.

Further, a fourth line, indicated with a dashed dotted curve 258 indicates the relative reduction of X-ray yield in percent.

According to an exemplary embodiment, as a cost-effective and simple solution, a multitude of single pixel sensors is placed at several positions within the field of X-rays emitted by the X-ray tube. For example a circular tube window, which his sufficiently transparent for X-rays emitted from the target, leads to a cone of X-rays emitted near the central axis. The rectangular field of view used for the imaging application is collimated from the cone, such that the sensor can be positioned within the X-ray beam without influencing the imaging application.

Figure 8:
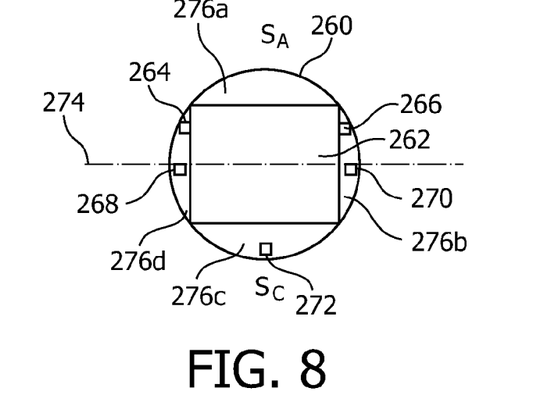
FIG. 8 schematically shows an exemplary embodiment of a sensor arrangement according to the invention.

As can be seen in FIG. 8, the at least one X-ray sensor 16 is arranged in segments 276a, 276b, 276c or 276d of the window, i.e. an area of the beam formation 30 indicated with a circle 260 in FIG. 7, which segments currently lie outside the field of investigation indicated with a rectangular 262, indicating the maximum size of the actually used part of the beam for imaging purposes.

For example, single pixel sensors permit a straightforward implementation of sensor readout.

This shall be explained with reference to FIG. 8. A circle 260 schematically indicates the X-ray window opening. Further, a rectangular 262 lying inside the circle 260 indicates the field of investigation, for example a maximum useful opening can correspond to a 300 by 380 millimeter rectangular detector format.

Further, in FIG. 8, the anode side is indicated with $S_A$, i.e. on the page with the Figures above the circle, and the cathode side is indicated with a $S_C$, i.e. below the circle.

Possible positions for sensors are indicated with little squares 264, 266, 268, and 270 as well as 272.

For example, the positions 264 and 266 towards the anode side are possible positions for heel-effect dose sensors.

The positions 268, 270, as well as 272 are possible positions for normal dose sensors. For a better understanding, the projection of a central axis is indicated with a dotted line 274.

Of course, it is also possible to position a sensor in the segment 276a above the rectangular 262 inside the circle 260. However, due to a low X-ray dose because of the heel-effect and the anode shade, depending on the position of the aperture 26 this position would in practice measure only a very low dose.

A sensor closer to the anode side, i.e. for a negative angle with respect to the central axis, will record less X-rays than a sensor closer to the cathode with an angle larger than 0 on account of the heel-effect. This difference in measured X-ray intensity is affected by the wear of the focal track and thus provides information which can be used to adapt the image processing steps dealing with heel-effect. Furthermore, the sensor data gives an insight into the wear of the focal track because the X-ray dose recorded by the sensor towards the anode will receive less X-rays for a degrading focal track.

Since the sensors measure the relative angular dependence of the X-ray yield, this method is undisturbed by absolute variations of the tube's X-ray output. Thus, the anode wear is detected independently from other aging effects which influence the X-ray yield, like contamination of the X-ray window or filament aging.

According to a further exemplary embodiment, it is also possible to provide a single sensor which thus gives information about the general dosage output of the X-ray source, in which the heel-effect and the contamination of the X-ray window are already considered.

According to a further exemplary embodiment, it is also possible to place a multi-pixel sensor at an off-axis position, i.e. relative to the central axis, at a negative angle, where the X-ray yield of the tube is most strongly affected by the heel-effect. This is shown in FIG. 9, where a multi-pixel sensor is indicated with the reference numeral 58.

For larger angles approaching the anode angle $(-\theta)\approx\alpha$, the inherent filtration significantly reduces the X-ray yield. For such angles, the X-ray efficiency is particularly sensitive to changes in the surface morphology of the X-ray target, in particular to cracks in the focal track.

The angular dependence of the X-ray yield is sampled by the multiple pixels and read out by a controller (not further shown) which collects the signals in each pixel. The result qualitatively behaves like the curve in FIG. 7 which serves as an indicator for the degree of anode wear. A fine sampling of the X-ray dose with a multi-pixel sensor increases the accuracy and therefore the confidence level of the lifetime prediction.

Figure 10:
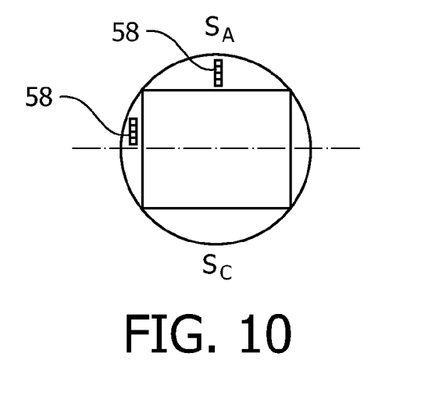
FIG. 10 schematically shows a further exemplary embodiment of a sensor arrangement.
Figure 11:
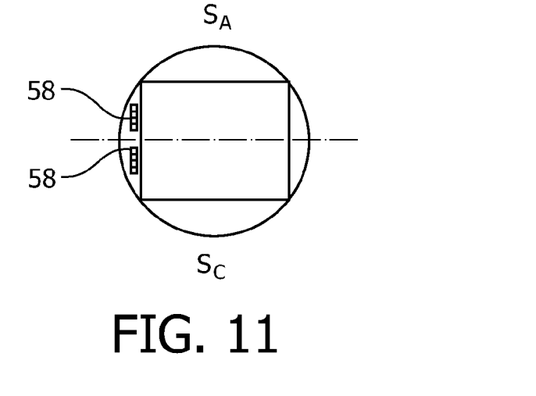
FIG. 11 schematically shows a further exemplary embodiment of a sensor arrangement.

According to a further example, one or more multi-pixel dose sensors 58 are arranged on the lateral side of the field of view, towards the anode side $A_S$, as shown in FIGS. 10 and 11.

It must be noted that the sensor does not interfere with the field of view needed for the imaging application, since it is placed at an off-axis position outside the field of view. This is possible, because the collimator or diaphragm typically limits the beam to a pyramid shape out of a cone shape thus providing "free to use segments."

For example, due to a number of geometrical restrictions on an X-ray sensor based on a rough estimation, the sensor should cover an angular range of $-\theta=[\alpha-2°,\alpha]$, where the inherent filtration is very prominent and the sensor is outside the field of view of field of investigation.

For example, assuming the centre is placed at a position at a distance of 5 cm from the focal track, the angular range of 2° is covered by a detector with a width of approximately 1.8 mm.

Figure 12:
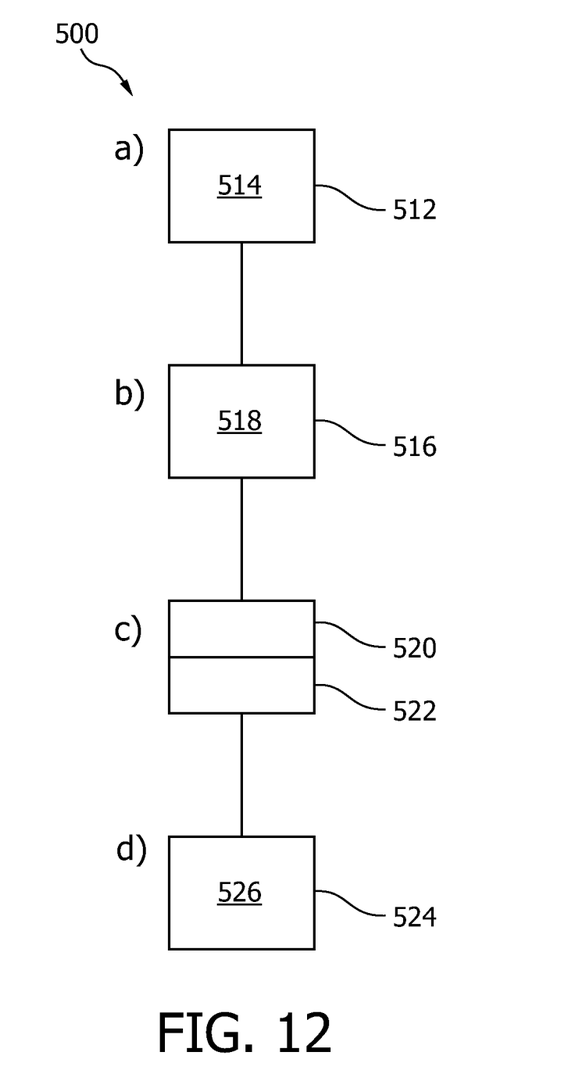
FIG. 12 schematically shows the basic steps of a method according to an exemplary embodiment of the invention.

In the following, with reference to FIG. 12, an exemplary embodiment of a method for determining changes in the X-ray emission yield of an X-ray source is described. A method 500 comprises the following steps:

First, in an emitting step 512, an X-ray beam 514 is emitted with an X-ray source. The X-ray source comprises a cathode to emit electrons towards an anode to generate X-ray radiation, wherein the X-ray beam has a beam formation with a central axis.

Next, in a measuring step 516, X-ray intensity 518 is measured for an angle between a specific direction of X-ray emission and the central axis with at least one X-ray sensor, which X-ray sensor is arranged within the beam formation of the X-ray beam.

Then, in a comparison step 520, the measured data is compared with stored data and analyzed 522.

Then, in a determining step 524, a dose degradation value 526 is determined based on the analysis of the comparison and analyzing step 520, 522.

It is noted that the emitting step 512 is also referred to as step a), the measuring step 516 as step b), the comparison step 520 together with the analyzing step 522 as step c), and the determining step 524 as step d).

According to a further aspect, in step b), a relative dose is measured at different positions.

According to a further aspect, in step c), a relative dose is measured over time at the same position.

According to a further aspect, in step d), changes of the heel-effect within the field of investigation are determined and correction filters in further image processing steps are adapted.

Figure 13:
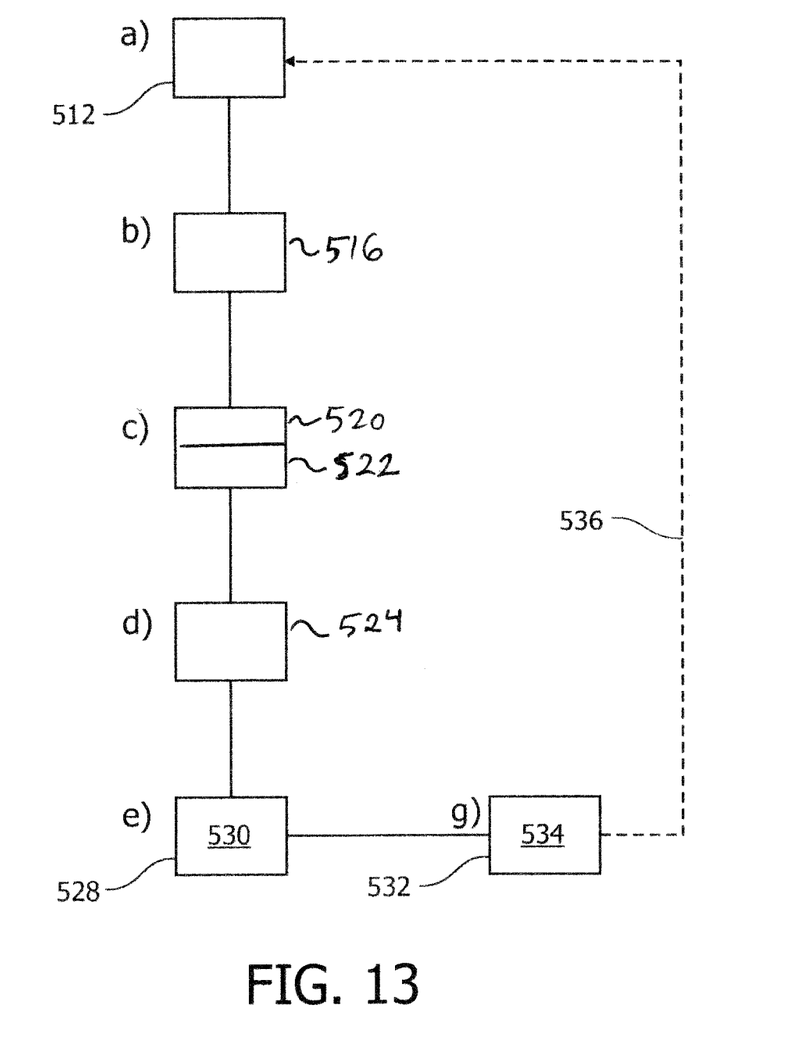
FIG. 13 shows a further exemplary embodiment of a method according to the invention.

According to a further exemplary embodiment shown in FIG. 13, following step d), a step e) is provided comprising calculating 528 new settings 530 of the X-ray source based on the degradation value for further X-ray generating. Further, a step g) is provided comprising updating 532 a yield factor 534 of the X-ray source.

For example, an automatic calculating of the new settings is provided.

According to a further aspect, the X-ray source parameters are automatically adjusted in order to correct for the reduction of the total X-ray yield of the source.

For example, the X-ray source comprises an X-ray window and the X-ray source settings are automatically adjusted in order to correct for anode roughening and contamination or staining of the X-ray window.

According to a further aspect, a relative angular dependence of the X-ray yield is measured and the anode wear is detected.

As also indicated in FIG. 13, according to a further aspect of the invention, the updated yield factor 534 can then be used for further X-ray radiation emitting steps, i.e. the updated yield factors 534 are provided in a loop-like manner which is indicated with a dotted arrow leaving the box 532 entering the box 512, with reference numeral 536.

Figure 14:
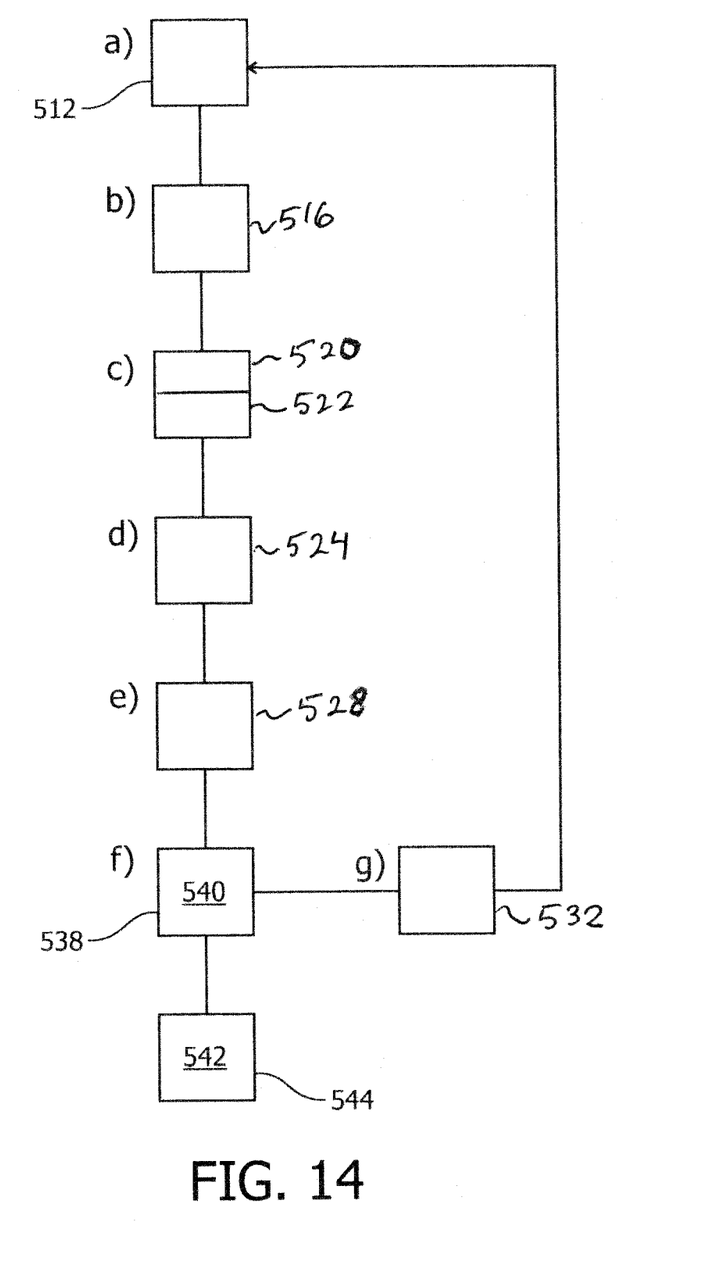
FIG. 14 shows a further exemplary embodiment of a method according to the invention.

According to a further aspect of the invention, shown in FIG. 14, before step g), a step f) is provided comprising comparing 538 the new settings of the X-ray source with predetermined values 540. Upon exceeding predetermined threshold values, further service measurements 542 are induced 544.

For example, a manual recalibration of a tube dose is induced. According to a further example, a tube replacement is induced.

Figure 15:
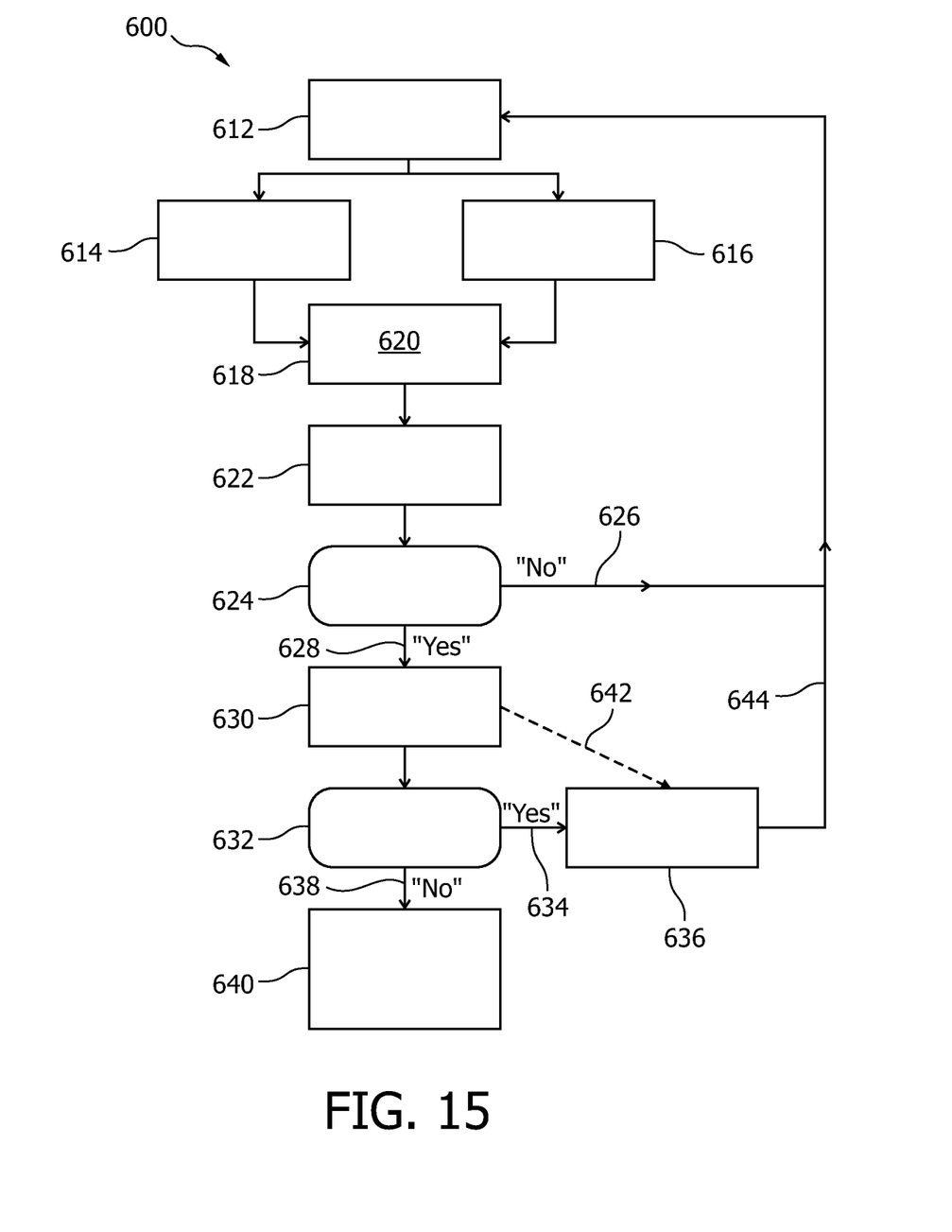
FIG. 15 shows a further exemplary embodiment of a method according to the invention.

According to a further exemplary embodiment illustrated in FIG. 15, a method is provided where an X-ray exposure 612 is provided followed by a data acquisition of the general dose sensor, indicated with box 614, and in parallel possibly by a data acquisition of the heel effect sensor indicated with box 616. The value or both values are then stored 618 in a data base 620. Next, a statistical analysis 622 is provided, for example a cusum method.

Then, it is determined 624 whether the tube dose degradation has been detected or not. If this is not the case, the X-ray exposure 612 can be started once again, which result "no" and the following loop-like performance is indicated with an arrow leaving the box 624 entering the box 612, which arrow is indicated with reference numeral 626. If dose degradation is detected, i.e. if the answer is "yes", then the next step is performed which is indicated by reference numeral 628 relating to an arrow pointing downwards from the box 624. A new tube yield table is calculated 630, or other parameters determining the relation between the electrical power input of the tube and the dose rate output of the tube.

Following, new set points are calculated to comply with dose regulations, for example by FDA dose regulations, and it is determined if the X-ray source can comply with these new settings, which determining step is indicated with reference numeral 632. If the answer is "yes", indicated with an arrow leaving to the right indicated with reference numeral 634, leading to updated settings 636 for the X-ray source. If the determining step 632 leads to the result "no", indicated with arrow 638, in a further step 640, an issue service call is performed for manual recalibration of tube dose or even for tube replacement.

Of course it is also possible to skip determination step 632 and to perform an automatic update 636/644 immediately after the calculation 632, which short-cut is indicated with a dotted arrow 642 from box 630 to box 636/line 644. Once the automatic update is performed in step 636, an X-ray exposure is once again performed, which is indicated by loop-like arrow 644.

As described with reference to FIG. 15, the X-ray dose sensors record the dose at each normal run of the X-ray tube. The measured data is compared to model data possibly generated according to a model of the heel-effect taking into account the tube voltage and average emission current of the X-ray tube. The measurement data is analyzed using statistical methods which detect significant variations of measured values to provide a higher robustness with respect to unavoidable fluctuations.

From such an analysis, an anode degradation parameter is extracted. When the degradation parameters exceed certain predefined limits, the tube dose and/or the image filter accounting for the heel-effect in the image processing are adjusted such that the reduced X-ray yield and the change in the intensity distribution are compensated. For example, a warning limit may be introduced for the anode degradation parameter. When the warning limit is reached, the user is informed that tube replacement is recommended in the near future. A possible scenario for performing an automated update is represented in FIG. 15. It must be mentioned that the present invention can be applied to all X-ray sources used in medical imaging systems; in particular where availability and reliability of the imaging system is critical, like C-arm systems for interventional surgery, CT, general X-ray in emergency rooms, etc. Furthermore, information on tube yield and emission characteristics like heel-effect and its ramifications with respect to the tube spectrum is of increasing importance for the acquisition of 3D data, either with CT scanners or C-arms, for example, and quantitative imaging protocols, for example used in the context of blood flow quantification, perfusion etc.

According to a further exemplary embodiment of a method, at least two sensors are used. In step b), at least one sensor is measuring the dose intensity in the bulk of the beam and at least one sensor is measuring the dose intensity in the heel-part of the beam. In step c), the difference between the tube intensities is compared to stored data for the analysis.

According to a further exemplary embodiment, a method is provided, wherein at least one multi-pixel sensor array is provided and positioned such that intensity values are measured for at least two directions in relation to the central axis. In step b), the at least one multi-pixel sensor array is measuring the dose intensity in the bulk of the beam, and the at least one multi-pixel sensor array is also measuring the dose intensity in the heel-part of the beam or at least one multi-pixel sensor stretches from the heel part into the bulk of the beam. In step c), the difference between the intensities of the pixels are compared to storage data for the analysis.

Figure 9:
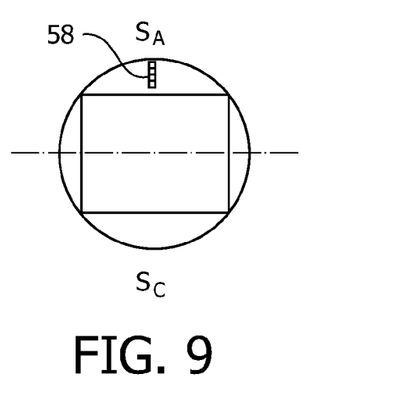
FIG. 9 schematically shows a further exemplary embodiment of a sensor arrangement.

As can be seen in FIG. 9 toll, for example, the multi-pixel dose sensor 58 is provided as a linear pixel arrangement.

According to a further aspect, the multi-pixel dose sensor is oriented in a direction between the anode side and the cathode side.

According to a further aspect, the multi-pixel dose sensor 58 is arranged on the anode side of the central axis.

According to a further aspect, as indicated in FIG. 11, the multi-pixel dose sensor 58 is positioned towards the anode side but on the lateral side of the field of investigation.

According to a further aspect, also shown in FIG. 10, at least two multi-pixel dose sensors 58 are provided.

According to a further exemplary embodiment not shown, the multi-pixel dose sensors are positioned on both lateral sides of the field of investigation.

According to a further exemplary embodiment not shown, at least one multi-pixel sensor array is provided towards the anode side and at least one multi-pixel sensor array is provided towards the cathode side.

According to a further aspect, at least one sensor is provided for heel-effect measurements and at least one sensor is provided for dose measurements.

According to a further aspect (not shown), the at least one X-ray sensor is X-ray transparent and the at least one sensor is arranged within the field of investigation.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an update turns an existing program into a program that uses the invention.

Further on, the computer program element might be able to provide all necessary steps to fulfil the procedure of an exemplary embodiment of the method as described above.

The computer program may be stored and/or distributed on a suitable medium, such as a magnetic or optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

According to a further exemplary embodiment of the present invention, a computer readable medium, such as a CD-ROM, is presented wherein the computer readable medium has a computer program element stored on it which computer program element is described by the preceding section.

It has to be noted that exemplary embodiments of the invention are described with reference to different subject matters. In particular, some exemplary embodiments are described with reference to apparatus type claims whereas other exemplary embodiments are described with reference to method type claims. However, a person skilled in the art will gather from the above and the following description that, unless otherwise notified, in addition to any combination of features belonging to one type of subject matter also any combination between features relating to different subject matters, in particular between features of the apparatus type claims and features of the method type claims, is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray intensity checking device comprising:
an X-ray source comprising:
   a cathode;
   an anode; and
   at least two X-ray sensors;
   wherein the cathode emits electrons towards the anode;
   wherein the anode comprises a target area on which the electrons impinge, generating X-ray radiation from which is formed a beam in which both sensors are disposed, said beam comprising a heel part of reduced X-ray intensity characteristic of a heel effect;
   wherein said source is configured for, via measurement by one or more sensors from among said at least two, determining X-ray intensity in said heel part and for, via measurement by at least one sensor from among said at least two, determining X-ray intensity within said beam but outside said heel part;
wherein an X-ray barrier is provided with an aperture for said forming;
wherein said beam has a beam formation defined by said aperture, extending back to said target area and extending forward past said aperture; and
wherein a sensor from among said at least one or more and a sensor from among said at least one are arranged within said beam formation; and an X-ray beam intensity checking processor configured for comparing said measurement from said heel part to said measurement outside said heel part.

2. A device according to claim 1, comprising a diaphragm that has an opening, which opening defines an actual field of investigation in terms of imaging, said at least two X-ray sensors being arranged outside this actual field of investigation.

3. A device according to claim 1, wherein the anode and the cathode are arranged inside a vacuum tube; wherein the vacuum tube comprises an X-ray window as the aperture in the X-ray barrier; and wherein said sensor from among said one or more and said sensor from among said at least one are arranged outside the vacuum tube.

4. A device according to claim 3, wherein said sensor from among said at least one or more and said sensor from among said at least one are arranged on said X-ray tube, outside of the X-ray window.

5. A device according to claim 1, wherein a sensor from among, collectively said one or more and said at least one, is a multi-pixel dose sensor.

6. The device of claim 1, said comparing comprising taking a difference between said measurement from said heel part and said measurement outside said heel part.

7. The device of claim 6, said processor being further configured for comparing said difference to a difference between respective other measurements from a heel part and from outside a heel part.

8. The device of claim 7, said processor being further configured for assessing dose degradation based on the difference-to-difference comparison.

9. The device of claim 8, said respective other measurements having been taken temporally with respect to said measurement from said heel part and said measurement outside said heel part such that an aging effect of said anode is reflected in an outcome of said comparison.

10. The device of claim 1, wherein said one or more sensors and said at least one sensor are arranged within said beam formation.

11. The device of claim 1, said determining, both in and outside said heel part, being performed for a relatively small angular segment in a specific direction of X-ray emission with respect to a central axis of said beam formation.

12. An X-ray source comprising:
a cathode;
an anode; and
at least two X-ray sensors;
wherein the cathode emits electrons towards the anode;
wherein the anode comprises a target area on which the electrons impinge, generating X-ray radiation from which is formed a beam in which both sensors are disposed, said beam comprising a heel part of reduced X-ray intensity characteristic of a heel effect;
wherein said source is configured for, via measurement by one or more sensors from among said at least two, determining X-ray intensity in said heel part and for, via measurement by at least one sensor from among said at least two, determining X-ray intensity within said beam but outside said heel part;
wherein an X-ray barrier is provided with an aperture for said forming;
wherein said beam has a beam formation defined by said aperture, extending back to said target area and extending forward past said aperture;
wherein said beam formation is characterizable as a maximum field of investigation, with respect to imaging, for that X-ray source's configuration;
wherein a sensor from among said at least one or more and a sensor from among said at least one are arranged within said beam formation,
wherein the anode is a rotating anode; and
wherein said sensor from among said at least one is positioned towards a cathode side with respect to a central axis of said beam formation and disposed for receiving directly from said target area, for the respective determining, X-rays of the generated radiation.

13. An X-ray imaging system comprising, for imaging, the X-ray source of claim 12, an X-ray detector, and a processing unit.

14. The X-ray system of claim 13, configured for clinical imaging of a medical subject.

15. An X-ray intensity checking device comprising:
an X-ray source comprising:
a cathode;
an anode; and
at least two X-ray sensors;
wherein the cathode emits electrons towards the anode;
wherein the anode comprises a target area on which the electrons impinge, generating X-ray radiation from which is formed a beam in which both sensors are disposed, said beam comprising a heel part of reduced X-ray intensity characteristic of a heel effect;
wherein said source is configured for, via measurement by one or more sensors from among said at least two, determining X-ray intensity in said heel part and for, via measurement by at least one sensor from among said at least two, determining X-ray intensity within said beam but outside said heel part;
wherein an X-ray barrier is provided with an aperture for said forming;
wherein said beam has a beam formation defined by said aperture, extending back to said target area and extending forward past said aperture, said beam formation having a central axis; and
wherein a sensor from among said at least one or more and a sensor from among said at least one are arranged within said beam formation; and
an X-ray beam intensity checking processor configured to measure X-ray intensity for a specific direction of X-ray emission with respect to said central axis, wherein said processor is configured to compare a difference between the two measurements with stored data and determine a dose degradation value based on the comparison.

16. The device of claim 15, further comprising an X-ray detector configured to record image information of an object of interest.

17. A non-transitory computer readable medium embodying a computer program for determining changes in the X-ray emission yield of an X-ray tube, said program having instructions executable by a processor for performing a plurality of acts, from among said plurality there being the acts of: a) emitting an X-ray beam with an X-ray source; which X-ray source comprises a cathode to emit electrons towards an anode to generate X-ray radiation; wherein the X-ray beam has a beam formation with a central axis; b) measuring X-ray intensity for a specific direction of X-ray emission with respect to the central axis with at least one X-ray sensor, which X-ray sensor is arranged within the beam formation of the X-ray beam; c) comparing the measured data with stored data and analyzing the measured data; and d) determining a dose degradation value based on the analysis of step c); wherein at least two sensors are used; wherein in step b), at least one sensor is measuring the dose intensity in the bulk of the beam; and at least one sensor is measuring the dose intensity in a heel part of the beam; and wherein in step c), the difference between the two intensities is compared to stored data for the analysis.

18. The computer readable medium according to claim 17, wherein, following step d), a step e) comprises calculating new settings of the X-ray source based on the degradation value for further X-ray generating; and a step g) is provided comprising updating a yield factor of the X-ray source.

19. The computer readable medium according to claim 18, wherein, before step g), a step f) is provided comprising comparing the new settings of the X-ray source with predetermined values; wherein upon exceeding predetermined threshold values, further service measurements are induced.

20. The computer readable medium according to claim 17, wherein at least one multi-pixel sensor array is provided and positioned such that intensity values are measured for at least two directions in relation to the central axis; wherein in step b), the at least one multi-pixel sensor array is measuring the dose intensity in the bulk of the beam, and the at least one multi-pixel sensor array is measuring the dose intensity in the heel part of the beam; wherein in step c), the difference between the two intensities is compared to stored data for the analysis.

21. The computer readable medium of claim 17, said anode comprising a target area, the emitting occurring in a path from said cathode to said target area, said target area being inclined in relation to said path, said measuring in the bulk of the stream comprising measuring in what is X-ray-intensity-wise the bulk of the stream.

22. The computer readable medium of claim 17, wherein said dose intensity measured by measuring the dose intensity in said bulk of said beam is on a cathode side with respect to said central axis.

* * * * *